United States Patent
Eberhardt et al.

(10) Patent No.: US 8,628,566 B2
(45) Date of Patent: Jan. 14, 2014

(54) STENTS FOR PROSTHETIC HEART VALVES

(75) Inventors: Carol E. Eberhardt, Fullerton, CA (US); Charles Tabor, St. Louis Park, MN (US); Carolyn Majkrzak, San Clemente, CA (US); Timothy R. Ryan, Shorewood, MN (US); Melissa Denton, Cleveland Heights, OH (US); Maria Botrous, Chino, CA (US); Janice L. Shay, Lake Forest, CA (US)

(73) Assignee: Medtronic, Inc., Minneapolis, MN (US)

( * ) Notice: Subject to any disclaimer, the term of this patent is extended or adjusted under 35 U.S.C. 154(b) by 174 days.

(21) Appl. No.: 12/358,980

(22) Filed: Jan. 23, 2009

(65) Prior Publication Data

US 2009/0292350 A1 Nov. 26, 2009

Related U.S. Application Data

(60) Provisional application No. 61/062,207, filed on Jan. 24, 2008.

(51) Int. Cl.
*A61F 2/06* (2013.01)

(52) U.S. Cl.
USPC ........ 623/1.24; 623/1.26; 623/2.17; 623/1.15

(58) Field of Classification Search
USPC ........... 623/1.24, 2.11, 2.14, 2.17–2.18, 1.16, 623/1.34, 1.15, 1.26
See application file for complete search history.

(56) References Cited

U.S. PATENT DOCUMENTS

| | | | |
|---|---|---|---|
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 3,868,956 A | 3/1975 | Alfidi et al. | |

(Continued)

FOREIGN PATENT DOCUMENTS

| CN | 2007-10074433 | 8/2007 |
|---|---|---|
| DE | 195 32 846 | 3/1997 |

(Continued)

OTHER PUBLICATIONS

U.S. Appl. No. 12/476,702, filed Jun. 2, 2009.

(Continued)

*Primary Examiner* — Thomas J Sweet
*Assistant Examiner* — Seema Mathew

(57) ABSTRACT

A stented valve including a stent structure including a generally tubular body portion having a first end, a second end, an interior area, a longitudinal axis, and a plurality of vertical wires extending generally parallel to the longitudinal axis around a periphery of the body portion, wherein the plurality of vertical wires includes multiple commissure wires and at least one structural wire positioned between adjacent commissure wires, and a plurality of V-shaped wire structures having a first end, a second end, and a peak between the first and second ends, wherein a first end of each V-shaped structure extends from a first vertical wire and a second end of each V-shaped structure extends from a second vertical wire that is adjacent to the first vertical wire, wherein each V-shaped structure is oriented so that its peak is facing in the same direction relative to the first and second ends of the body portion, and a valve structure including a plurality of leaflets attached to the stent structure within the tubular body portion.

19 Claims, 9 Drawing Sheets

(56) References Cited

U.S. PATENT DOCUMENTS

| | | | |
|---|---|---|---|
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,265,694 | A | 5/1981 | Boretos |
| 4,297,749 | A | 11/1981 | Davis et al. |
| 4,343,048 | A | 8/1982 | Ross et al. |
| 4,345,340 | A | 8/1982 | Rosen |
| 4,425,908 | A | 1/1984 | Simon |
| 4,470,157 | A | 9/1984 | Love |
| 4,501,030 | A | 2/1985 | Lane |
| 4,574,803 | A | 3/1986 | Storz |
| 4,580,568 | A | 4/1986 | Gianturco |
| 4,592,340 | A | 6/1986 | Boyles |
| 4,610,688 | A | 9/1986 | Silvestrini et al. |
| 4,647,283 | A | 3/1987 | Carpentier et al. |
| 4,648,881 | A | 3/1987 | Carpentier et al. |
| 4,665,906 | A | 5/1987 | Jervis |
| 4,681,908 | A | 7/1987 | Broderick et al. |
| 4,710,192 | A | 12/1987 | Liotta et al. |
| 4,787,899 | A | 11/1988 | Lazarus |
| 4,796,629 | A | 1/1989 | Grayzel |
| 4,797,901 | A | 1/1989 | Goerne et al. |
| 4,819,751 | A | 4/1989 | Shimada et al. |
| 4,834,755 | A | 5/1989 | Silvestrini et al. |
| 4,856,516 | A | 8/1989 | Hillstead |
| 4,872,874 | A | 10/1989 | Taheri |
| 4,878,495 | A | 11/1989 | Grayzel |
| 4,878,906 | A | 11/1989 | Lindemann et al. |
| 4,883,458 | A | 11/1989 | Shiber |
| 4,909,252 | A | 3/1990 | Goldberger |
| 4,917,102 | A | 4/1990 | Miller et al. |
| 4,922,905 | A | 5/1990 | Strecker |
| 4,994,077 | A | 2/1991 | Dobben |
| 5,002,559 | A | 3/1991 | Tower |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,085,635 | A | 2/1992 | Cragg |
| 5,089,015 | A | 2/1992 | Ross |
| 5,152,771 | A | 10/1992 | Sabbaghian et al. |
| 5,161,547 | A | 11/1992 | Tower |
| 5,163,953 | A | 11/1992 | Vince |
| 5,167,628 | A | 12/1992 | Boyles |
| 5,217,483 | A | 6/1993 | Tower |
| 5,232,445 | A | 8/1993 | Bonzel |
| 5,272,909 | A | 12/1993 | Nguyen et al. |
| 5,295,958 | A | 3/1994 | Shturman |
| 5,327,774 | A | 7/1994 | Nguyen et al. |
| 5,332,402 | A | 7/1994 | Teitelbaum |
| 5,350,398 | A | 9/1994 | Pavcnik et al. |
| 5,370,685 | A | 12/1994 | Stevens |
| 5,389,106 | A | 2/1995 | Tower |
| 5,397,351 | A | 3/1995 | Pavcnik et al. |
| 5,411,552 | A | 5/1995 | Andersen et al. |
| 5,415,633 | A | 5/1995 | Lazarus et al. |
| 5,431,676 | A | 7/1995 | Dubrul et al. |
| 5,443,446 | A | 8/1995 | Shturman |
| 5,480,424 | A | 1/1996 | Cox |
| 5,489,294 | A | 2/1996 | McVenes et al. |
| 5,489,297 | A | 2/1996 | Duran |
| 5,496,346 | A | 3/1996 | Horzewski et al. |
| 5,500,014 | A | 3/1996 | Quijano et al. |
| 5,507,767 | A | 4/1996 | Maeda et al. |
| 5,545,209 | A | 8/1996 | Roberts et al. |
| 5,545,211 | A | 8/1996 | An et al. |
| 5,545,214 | A | 8/1996 | Stevens |
| 5,554,185 | A | 9/1996 | Block et al. |
| 5,575,818 | A | 11/1996 | Pinchuk |
| 5,580,922 | A | 12/1996 | Park et al. |
| 5,591,195 | A | 1/1997 | Taheri et al. |
| 5,609,626 | A | 3/1997 | Quijano et al. |
| 5,645,559 | A | 7/1997 | Hachtman et al. |
| 5,667,523 | A | 9/1997 | Bynon et al. |
| 5,674,277 | A | 10/1997 | Freitag |
| 5,702,368 | A | 12/1997 | Stevens et al. |
| 5,713,953 | A | 2/1998 | Vallana et al. |
| 5,716,417 | A | 2/1998 | Girard et al. |
| 5,746,709 | A | 5/1998 | Rom et al. |
| 5,749,890 | A | 5/1998 | Shaknovich |
| 5,766,151 | A | 6/1998 | Valley et al. |
| 5,782,809 | A | 7/1998 | Umeno et al. |
| 5,800,456 | A | 9/1998 | Maeda et al. |
| 5,800,508 | A | 9/1998 | Goicoechea et al. |
| 5,817,126 | A | 10/1998 | Imran |
| 5,824,041 | A | 10/1998 | Lenker et al. |
| 5,824,043 | A | 10/1998 | Cottone, Jr. |
| 5,824,053 | A | 10/1998 | Khosravi et al. |
| 5,824,056 | A | 10/1998 | Rosenberg |
| 5,824,061 | A | 10/1998 | Quijano et al. |
| 5,824,064 | A | 10/1998 | Taheri |
| 5,855,597 | A | 1/1999 | Jayaraman |
| 5,855,601 | A | 1/1999 | Bessler et al. |
| 5,860,996 | A | 1/1999 | Urban et al. |
| 5,861,028 | A | 1/1999 | Angell |
| 5,868,783 | A | 2/1999 | Tower |
| 5,891,191 | A | 4/1999 | Stinson |
| 5,906,619 | A | 5/1999 | Olson et al. |
| 5,913,842 | A | 6/1999 | Boyd et al. |
| 5,925,063 | A | 7/1999 | Khosravi |
| 5,957,949 | A | 9/1999 | Leonhardt et al. |
| 5,968,068 | A | 10/1999 | Dehdashtian et al. |
| 5,984,957 | A | 11/1999 | Laptewicz, Jr. et al. |
| 5,997,573 | A | 12/1999 | Quijano et al. |
| 6,022,370 | A | 2/2000 | Tower |
| 6,027,525 | A | 2/2000 | Suh et al. |
| 6,029,671 | A | 2/2000 | Stevens et al. |
| 6,042,589 | A | 3/2000 | Marianne |
| 6,042,598 | A | 3/2000 | Tsugita et al. |
| 6,042,607 | A | 3/2000 | Williamson, IV |
| 6,051,014 | A | 4/2000 | Jang |
| 6,059,809 | A | 5/2000 | Amor et al. |
| 6,110,201 | A | 8/2000 | Quijano et al. |
| 6,146,366 | A | 11/2000 | Schachar |
| 6,159,239 | A | 12/2000 | Greenhalgh |
| 6,162,245 | A | 12/2000 | Jayaraman |
| 6,171,335 | B1 | 1/2001 | Wheatley et al. |
| 6,200,336 | B1 | 3/2001 | Pavcnik et al. |
| 6,203,550 | B1 | 3/2001 | Olson |
| 6,210,408 | B1 | 4/2001 | Chandrasekaran et al. |
| 6,218,662 | B1 | 4/2001 | Tchakarov et al. |
| 6,221,006 | B1 | 4/2001 | Dubrul et al. |
| 6,221,091 | B1 | 4/2001 | Khosravi |
| 6,245,102 | B1 | 6/2001 | Jayaraman |
| 6,248,116 | B1 | 6/2001 | Chevillon et al. |
| 6,258,114 | B1 | 7/2001 | Konya et al. |
| 6,258,115 | B1 | 7/2001 | Dubrul |
| 6,258,120 | B1 | 7/2001 | McKenzie et al. |
| 6,277,555 | B1 | 8/2001 | Duran et al. |
| 6,299,637 | B1 | 10/2001 | Shaolian et al. |
| 6,302,906 | B1 | 10/2001 | Goicoechea et al. |
| 6,309,382 | B1 | 10/2001 | Garrison et al. |
| 6,309,417 | B1 | 10/2001 | Spence et al. |
| 6,338,735 | B1 | 1/2002 | Stevens |
| 6,348,063 | B1 | 2/2002 | Yassour et al. |
| 6,350,277 | B1 | 2/2002 | Kocur |
| 6,352,708 | B1 | 3/2002 | Duran et al. |
| 6,371,970 | B1 | 4/2002 | Khosravi et al. |
| 6,371,983 | B1 | 4/2002 | Lane |
| 6,380,457 | B1 | 4/2002 | Yurek et al. |
| 6,398,807 | B1 | 6/2002 | Chouinard et al. |
| 6,409,750 | B1 | 6/2002 | Hyodoh et al. |
| 6,425,916 | B1 | 7/2002 | Garrison et al. |
| 6,440,164 | B1 | 8/2002 | DiMatteo et al. |
| 6,454,799 | B1 * | 9/2002 | Schreck ............... 623/2.18 |
| 6,458,153 | B1 | 10/2002 | Bailey et al. |
| 6,461,382 | B1 * | 10/2002 | Cao ............... 623/2.19 |
| 6,475,239 | B1 | 11/2002 | Campbell et al. |
| 6,482,228 | B1 | 11/2002 | Norred |
| 6,488,704 | B1 | 12/2002 | Connelly et al. |
| 6,494,909 | B2 | 12/2002 | Greenhalgh |
| 6,503,272 | B2 | 1/2003 | Duerig et al. |

(56) References Cited

U.S. PATENT DOCUMENTS

| | | |
|---|---|---|
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B2 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Pease et al. |
| 6,736,846 B2 | 5/2004 | Cox |
| 6,752,828 B2 | 6/2004 | Thornton |
| 6,769,434 B2 | 8/2004 | Liddicoat et al. |
| 6,786,925 B1 | 9/2004 | Buchanan et al. |
| 6,790,229 B1 | 9/2004 | Berreklouw |
| 6,792,979 B2 | 9/2004 | Konya et al. |
| 6,797,002 B2 | 9/2004 | Spence et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Strecter |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 * | 4/2007 | Figulla et al. ............... 623/2.1 |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,510,575 B2 * | 3/2009 | Spenser et al. ............... 623/2.18 |
| 7,544,206 B2 | 6/2009 | Cohn et al. |
| 7,556,646 B2 | 7/2009 | Yang et al. |
| 7,947,075 B2 * | 5/2011 | Goetz et al. ............... 623/2.18 |
| 7,993,394 B2 * | 8/2011 | Hariton et al. ............... 623/2.17 |
| 8,052,750 B2 * | 11/2011 | Tuval et al. ............... 623/2.17 |
| 8,075,611 B2 * | 12/2011 | Millwee et al. ............... 623/1.24 |
| 8,236,045 B2 * | 8/2012 | Benichou et al. ............... 623/1.26 |
| 8,348,998 B2 * | 1/2013 | Pintor et al. ............... 623/2.11 |
| 8,398,704 B2 * | 3/2013 | Straubinger et al. ............... 623/1.15 |
| 8,403,983 B2 * | 3/2013 | Quadri et al. ............... 623/2.17 |
| 8,454,685 B2 * | 6/2013 | Hariton et al. ............... 623/2.17 |
| 8,460,366 B2 * | 6/2013 | Rowe ............... 623/1.36 |
| 8,465,540 B2 * | 6/2013 | Straubinger et al. ............... 623/2.1 |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |

(56) References Cited

U.S. PATENT DOCUMENTS

| | | |
|---|---|---|
| 2003/0149478 A1 | 8/2003 | Figulla et al. |
| 2003/0153974 A1 | 8/2003 | Spenser et al. |
| 2003/0176914 A1* | 9/2003 | Rabkin et al. ............... 623/1.15 |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2004/0034411 A1 | 2/2004 | Quijano et al. |
| 2004/0039436 A1* | 2/2004 | Spenser et al. ............... 623/1.13 |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Seguin et al. |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty et al. |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz et al. |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075713 A1* | 4/2005 | Biancucci et al. ............ 623/1.11 |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075728 A1* | 4/2005 | Nguyen et al. ............... 623/2.17 |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0182483 A1* | 8/2005 | Osborne et al. ............... 623/1.24 |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1* | 10/2005 | Paine ............ 623/1.24 |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0009841 A1 | 1/2006 | McGuckin et al. |
| 2006/0025857 A1* | 2/2006 | Bergheim et al. ............ 623/2.18 |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0149360 A1* | 7/2006 | Schwammenthal et al. .. 623/1.24 |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2006/0287717 A1* | 12/2006 | Rowe et al. ............... 623/2.11 |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038291 A1* | 2/2007 | Case et al. ............... 623/1.16 |
| 2007/0043435 A1 | 2/2007 | Seguin et al. |
| 2007/0051377 A1 | 3/2007 | Douk et al. |
| 2007/0073392 A1 | 3/2007 | Heyninck-Jantz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |

(56) References Cited

U.S. PATENT DOCUMENTS

| | | |
|---|---|---|
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004688 A1 | 1/2008 | Spenser et al. |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1* | 3/2008 | Tuval et al. ............... 623/2.1 |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1* | 6/2008 | Benichou et al. ............ 623/1.26 |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1* | 10/2008 | Straubinger et al. ......... 623/2.36 |
| 2008/0262593 A1 | 10/2008 | Ryan et al. |
| 2008/0275540 A1* | 11/2008 | Wen ............... 623/1.26 |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0138079 A1 | 5/2009 | Tuval et al. |
| 2009/0164004 A1 | 6/2009 | Cohn |
| 2009/0171447 A1 | 7/2009 | Von Segesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0240264 A1 | 9/2009 | Tuval et al. |
| 2009/0240320 A1 | 9/2009 | Tuval |
| 2009/0270972 A1* | 10/2009 | Lane ............... 623/1.14 |
| 2009/0287299 A1 | 11/2009 | Tabor et al. |
| 2010/0011564 A1 | 1/2010 | Millwee et al. |
| 2010/0018447 A1 | 1/2010 | Holecek et al. |
| 2010/0023120 A1 | 1/2010 | Holecek et al. |
| 2010/0036484 A1 | 2/2010 | Hariton et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145435 A1* | 6/2010 | Voinov et al. ............... 623/1.26 |
| 2010/0217382 A1* | 8/2010 | Chau et al. ............... 623/1.26 |
| 2010/0249894 A1* | 9/2010 | Oba et al. ............... 623/1.11 |
| 2011/0125244 A1* | 5/2011 | Roeder et al. ............... 623/1.11 |
| 2011/0224780 A1* | 9/2011 | Tabor et al. ............... 623/1.24 |
| 2011/0257729 A1* | 10/2011 | Spenser et al. ............... 623/1.26 |
| 2012/0078347 A1* | 3/2012 | Braido et al. ............... 623/1.26 |
| 2012/0078357 A1* | 3/2012 | Conklin ............... 623/2.18 |

FOREIGN PATENT DOCUMENTS

| | | |
|---|---|---|
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 48 814 | 9/2000 |
| DE | 100 49 812 | 4/2002 |
| DE | 100 49 813 | 4/2002 |
| DE | 100 49 815 | 4/2002 |
| EP | 0103546 | 3/1984 |
| EP | 0597967 | 12/1994 |
| EP | 0850607 | 7/1998 |
| EP | 1057459 A1 | 6/2000 |
| EP | 1057460 A1 | 6/2000 |
| EP | 1088529 | 4/2001 |
| EP | 1255510 | 11/2002 |
| EP | 0937439 B1 | 9/2003 |
| EP | 1340473 | 9/2003 |
| EP | 0819013 | 6/2004 |
| FR | 2788217 | 12/1999 |
| GB | 2056023 | 3/1981 |
| GB | 2433700 | 12/2007 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |
| WO | 2005/027790 | 3/2005 |

(56) References Cited

FOREIGN PATENT DOCUMENTS

| WO | 2005/046528 | 5/2005 |
|---|---|---|
| WO | 2008/047354 | 4/2008 |
| WO | 2008/079962 | 7/2008 |
| WO | 2008/100599 | 8/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | WO 2009/042196 A2 | 4/2009 |
| WO | 2009/061389 | 5/2009 |
| WO | 2009/091509 | 7/2009 |

OTHER PUBLICATIONS

U.S. Appl. No. 12/711,289, filed Feb. 24, 2010.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," in: Topol EJ, ed. Textbook of Interventional Cardiology. Volume II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pasupati et al., "Transcatheter Aortic Valve Implantation Complicated by Acute Structural Valve Failure Requiring Immediate Valve in Valve Implantation," Heart, Lung and Circulation 2010; doi:10. 1016/j.hlc.2010.05.006.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Webb, et al., "Percutaneous Aortic Valve Implantation Retrograde from the Femoral Artery," Circulation (2006), 113;842-850.
Expert report of Dr. Nigel Buller, dated Jan. 12, 2009, Edwards' United Kingdom action for invalidity, Claim No. HC 08C00934 (83 pages).
Expert report of Dr. Nigel Buller, non-confidential annex—infringement, dated Jan. 12, 2009, Edwards' United Kingdom action for invalidity, Claim No. HC 08C00934 (12 pages).
Expert report of Dr. Rodolfo Quijano, dated Jan. 9, 2009, *Edwards' LifeSciences v. Cook Biotech Incorporated*, United Kingdom action for invalidity, Claim No. HC 08C00934 (18 pages).
First Expert report of Prof. David Williams, dated Jan. 12, 2009, Edwards' United Kingdom action for invalidity, Claim No. HC 08C00934 (41 pages).
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), *Corevalve, Inc. v. Edwards Lifesciences AG and Edwards Lifesciences PVT, Inc.*, High Court of Justice—Chancery Division Patents Court, United Kingdom, Case No. HC-07-001243.
European Patent Office Communication in Application No. 09 704 087.7-2320, Dated Nov. 30, 2012, 5 pages.

* cited by examiner

STENTS FOR PROSTHETIC HEART VALVES

CROSS-REFERENCE TO RELATED APPLICATION

The present application claims priority to U.S. Provisional Application No. 61/062,207, filed Jan. 24, 2008, and titled "Delivery Systems and Methods of Implantation for Prosthetic Heart Valves", the entire contents of which is incorporated herein by reference in its entirety.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a very small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously-delivered prosthetic heart valves have been suggested having a generally similar configuration, such as by Bonhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons that are sometimes used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Although there have been advances in percutaneous valve replacement techniques and devices, there is a continued desire to provide different designs of cardiac valves that can be implanted in a minimally invasive and percutaneous manner.

SUMMARY

The replacement heart valves of the invention each include a stent to which a valve structure is attached. The stents of the invention include a wide variety of structures and features that can be used alone or in combination with features of other stents of the invention. In particular, these stents provide a number of different docking and/or anchoring structures that are conducive to percutaneous delivery thereof. Many of the structures are thus compressible to a relatively small diameter for percutaneous delivery to the heart of the patient, and then are expandable either via removal of external compressive forces (e.g., self-expanding stents), or through application of an outward radial force (e.g., balloon expandable stents). The devices delivered by the delivery systems described herein can be used to deliver stents, valved stents, or other interventional devices such as ASD (atrial septal defect) closure devices, VSD (ventricular septal defect) closure devices, or PFO (patent foramen ovale) occluders.

Methods for insertion of the replacement heart valves of the invention include delivery systems that can maintain the stent structures in their compressed state during their insertion and allow or cause the stent structures to expand once they are in their desired location. In addition, delivery methods of the invention can include features that allow the stents to be retrieved for removal or relocation thereof after they have been deployed or partially deployed from the stent delivery systems. The methods may include implantation of the stent structures using either an antegrade or retrograde approach. Further, in many of the delivery approaches of the invention, the stent structure is rotatable in vivo to allow the stent structure to be positioned in a desired orientation.

One embodiment of a stent of the invention comprises a tubular wire structure including multiple longitudinal wires that extend generally parallel to the longitudinal axis of the stent. The wires are spaced from each other around the periphery of the stent. The stent further includes tissue attachment features, such as commissure attachment posts. In one embodiment, the stent includes three commissure attachment posts, where each of the posts is used as a connection location for one of the commissures of a tri-leaflet valve that will be attached thereto. Alternatively, more or less than three posts can be provided for a valve having more or less than three leaflets, respectively. The stent further includes multiple V-shaped wire structures between a pair of wires and/or between a wire and an adjacent attachment post. In one embodiment, the stent includes three V-shaped wires that are longitudinally spaced from each other along the height of the stent between each adjacent pair of wires or between a wire and an adjacent post. There may alternatively be more or less than three V-shaped wires spaced longitudinally from each other.

A first end of each V-shaped wire extends from a first end of an attachment post or wire, and a second end of wire extends from the first end of an adjacent wire or attachment post. In this way, a peak of each V-shaped wire will be positioned generally in the center of the space between adjacent longitudinal wires, and will be directed toward a second or inlet end of the stent. All or some of the wires can be flared at least slightly outward relative to the outer tubular shape of the stent, thereby creating integrated flange structures that can be used to capture the native leaflets when the stent is implanted in a patient. Each wire is spaced longitudinally from a corresponding wire, and each wire is spaced longitudinally from a corresponding wire.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
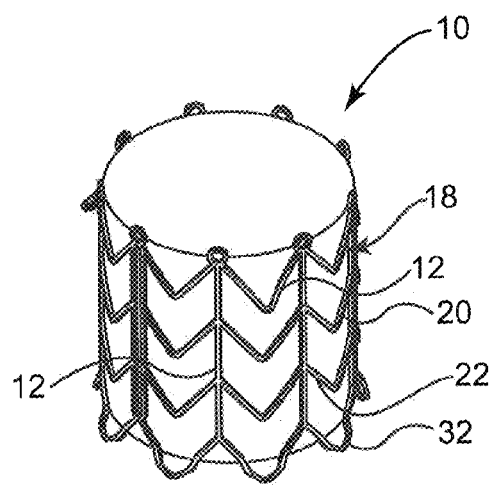
FIG. 1 is a perspective view of an embodiment of a stent in accordance with the invention.
Figure 2:
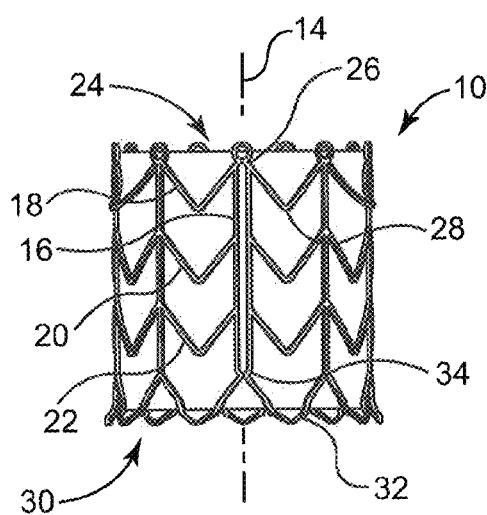
FIG. 2 is a front view of the stent of FIG. 1.

As referred to herein, the prosthetic heart valves used in accordance with the various devices and methods of heart valve delivery may include a wide variety of different configurations, such as a prosthetic heart valve having tissue leaflets or a synthetic heart valve having polymeric, metallic, or tissue-engineered leaflets, and can be specifically configured for replacing any heart valve. That is, while much of the description herein refers to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example.

Although each of the valves used with the delivery devices and methods described herein would typically include leaflets attached within an interior area of a stent, the leaflets are not shown in many of the illustrated embodiments for clarity purposes. In general, the stents described herein include a support structure comprising a number of strut or wire portions arranged relative to each other to provide a desired compressibility, strength, and leaflet attachment zone(s) to the heart valve. Other details on particular configurations of the stents of the invention are also described below; however, in general terms, stents of the invention are generally tubular support structures, and leaflets will be secured within the inner portion of the support structure to provide a valved stent. The leaflets can be formed from a variety of materials, such as autologous tissue, xenograph material, or synthetics as are known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled to the support structure of the stent. In another alternative, the stent and leaflets can be fabricated at the same time, such as may be accomplished using high strength nano-manufactured NiTi films of the type produced at Advanced Bio Prosthetic Surfaces Ltd. (ABPS) of San Antonio, Tex., for example. The support structures are generally configured to accommodate three leaflets; however, the replacement prosthetic heart valves of the invention can be configured to incorporate more or less than three leaflets.

In more general terms, the combination of a support structure with one or more leaflets can assume a variety of other configurations that differ from those shown and described, including any known prosthetic heart valve design. In certain embodiments of the invention, the support structure with leaflets utilize certain features of known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodyamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105: 775-558; Bonhoeffer, P., "Transcatheter Implantation of a Bovine Valve in Pulmonary Position, a Lamb Study", Circulation, 2000:102:813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Orientation and positioning of the stents of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. For example, when aligning the stents of the invention with native anatomical structures, they should be aligned so as to not block the coronary arteries, and native mitral or tricuspid valves should be aligned relative to the anterior leaflet and/or the trigones/commissures.

Some embodiments of the support structures of the stents described herein can be a series of wires or wire segments arranged so that they are capable of transitioning from a collapsed state to an expanded state. In some embodiments, a number of individual wires comprising the support structure can be formed of a metal or other material. These wires are arranged in such a way that a support structure allows for folding or compressing to a contracted state in which its internal diameter is greatly reduced from its internal diameter when it is in an expanded state. In its collapsed state, such a support structure with attached valves or leaflets can be mounted over a delivery device, such as a balloon catheter, for example. The support structure is configured so that it can be changed to its expanded state when desired, such as by the expansion of a balloon catheter. The delivery systems used for such a stent should be provided with degrees of rotational and axial orientation capabilities in order to properly position the stent at its desired location within the patient.

The wires of the support structure of the stents in other embodiments can alternatively be formed from a shape memory material such as a nickel titanium alloy (e.g., Nitinol). With this material, the support structure is self-expandable from a contracted state to an expanded state, such as by the application of heat, energy, and the like, or by the removal of external forces (e.g., compressive forces). This support structure can also be repeatedly compressed and re-expanded without damaging the structure of the stent. In addition, the support structure of such an embodiment may be laser cut from a single piece of material or may be assembled from a number of different components. For these types of stent structures, one example of a delivery system that can be used includes a catheter with a retractable sheath that covers the stent until it is to be deployed, at which point the sheath can be retracted to allow the stent to expand.

Referring now to the Figures, wherein the components are labeled with like numerals throughout the several Figures, and initially to FIGS. 1-4, an exemplary embodiment of a stent 10 is illustrated. Stent 10 may be referred to as a sub-coronary stent for use in replacement of the aortic valve in that it is preferably relatively short to enable stent placement below the coronaries. Stent 10 may be made of a self-expanding material, such as Nitinol, for example. In one embodiment, the stent 10 is generally tubular in shape and can be approximately 25 mm long, for example, although it can be longer or shorter than 25 mm, depending on the anatomy of the patient, the preferences of the surgeon, and other factors. The stent 10 includes multiple longitudinal or vertical wires 12 that extend generally parallel to a longitudinal axis 14 of the stent. The wires 12 are spaced from each other around the periphery of the generally tubular shape of the stent 10. Stent 10 further includes features to which tissue can be attached to make the stent into a valve, such as commissure attachment posts 16 that can be approximately 18 mm long, for example. The commissure attachment posts 16 each include two longitudinal wires that are spaced closer to each other than the spacing of the wires 12 from each other.

In this embodiment, stent 10 includes three commissure attachment posts 16, where each of the posts 16 is used as a connection location for one of the commissures of a tri-leaflet valve that will be attached thereto. Alternatively, more or less than three posts 16 can be provided for a valve having more or less than three leaflets, respectively. In addition to providing the structure for attachment of commissures, the posts 16 also provide additional stability to the stent 10. The wires 12 and posts 16 are preferably spaced at generally the same distance from each other around the periphery of the stent 10, although it is contemplated that some of the wires 12 and/or posts 16 can be spaced at different distances from each other around the periphery of the stent 10. Further, the specific illustrated embodiment of stent 10 includes two wires 12 positioned between two commissure attachment posts 16, although an alternate embodiment may include more or less wires 12 between adjacent commissure posts 16. However, the specific embodiment of stent 10 illustrated in FIGS. 1-4 comprises nine longitudinal structures around its periphery, including six longitudinal wires 12 and three commissure attachment posts 16.

Stent 10 further includes multiple V-shaped wire structures between a pair of wires 12 and/or between a wire 12 and an adjacent attachment post 16. As shown, the stent 10 includes three wires 18, 20, 22 that are longitudinally spaced from each other along the height of the stent 10 between each adjacent pair of wires 12 or between a wire 12 and an adjacent post 16. The size and shape of the wires 18, 20, 22 determines the spacing between adjacent longitudinal structures of the stent 10, which is generally uniform around the periphery of the stent, as discussed above. Although the stent 10 includes three of these V-shaped wires 18, 20, 22 that are spaced longitudinally from each other between adjacent vertical wire structures, there may be more or less than three V-shaped wires spaced longitudinally from each other.

Wires 18 are positioned at a first or outlet end 24 of the stent 10. A first end of each wire 18 extends from a first end 26 of an attachment post 16 or wire 12, and a second end of wire 18 extends from the first end 26 of an adjacent wire 12 or attachment post 16. In this way, a peak 28 of each wire 18 will be positioned generally in the center of the space between adjacent longitudinal wires, and will be directed toward a second or inlet end 30 of the stent 10. All or some of the wires 18 can be flared at least slightly outward relative to the outer tubular shape of the stent 10, thereby creating integrated flange structures that can be used to capture the native leaflets when the stent is implanted in a patient. Each wire 20 is spaced longitudinally from a corresponding wire 18, and each wire 22 is spaced longitudinally from a corresponding wire 20.

Additional wire structures 32 are positioned at the second end 30 of the stent 10 to correspond with each set of wires 18, 20, 22. In particular, each wire structure 32 is generally V-shaped, where the peak of each of the "V" structures is oriented in generally the same direction as the peaks of the wires 18, 20, 22. A first end of each wire structure 32 extends from a second end 34 of an attachment post 16 or wire 12, and a second end of wire structure 32 extends from the second end 34 of an adjacent wire 12 or attachment post 16. All or some of the wire structures 32 are flared at least slightly outward relative to the outer tubular shape of the stent 10. The amount and angle at which the wire structures extend relative to the tubular outer shape of the stent can be selected for capturing native patient anatomical features. In addition, this flare of the wire structures 32 can help to prevent or minimize leakage between the implant and the native annulus and/or to provide a physical and/or visual docking feature to secure the stent 10 against a wall of an opening in the heart to prevent migration of the stent, for example.

The stent 10 has a relatively high-density strut pattern to contain leaflets within the inner stent area during crimping of the stent. That is, while the exact number of longitudinal wires and V-shaped wires can vary somewhat from that illustrated in the Figures, it is preferable that the number of wires provided is sufficient to keep the leaflet material from becoming compressed and potentially damaged between the stent struts during the crimping process or from protruding beyond the periphery of the stent when it is in a crimped condition.

The first end 26 of all or some of the wires 12 and posts 16 can further include a loop or eyelet 36 that can be used for attachment to a delivery system and/or tissue valve, for example. The eyelets 36 can be in the same general plane as the outer tubular shape of the stent 10, or they can be directed at least slightly inward toward the central area of the stent or at least slightly outward relative to the outer tubular surface of the stent. The single-sided eyelet attachment end can be used in a resheathable delivery system for both antegrade and retrograde procedures, for example. Attachment end crown reducers can optionally be added to the stent to reduce the attachment crown number, although the stent would be lengthened at least slightly by such a modification.

Figure 4:
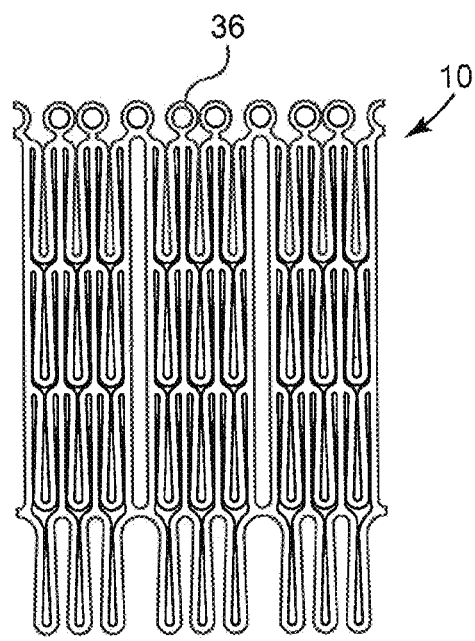
FIG. 4 is a top view of a cutting pattern for the stent of FIG. 1.
Figure 3:
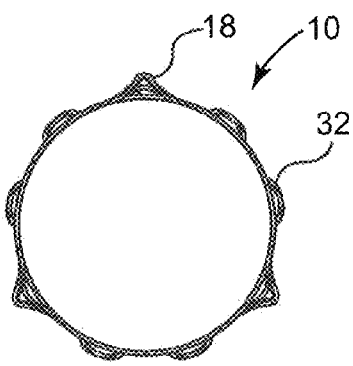
FIG. 3 is a top view of the stent of FIG. 1.
Figure 5:
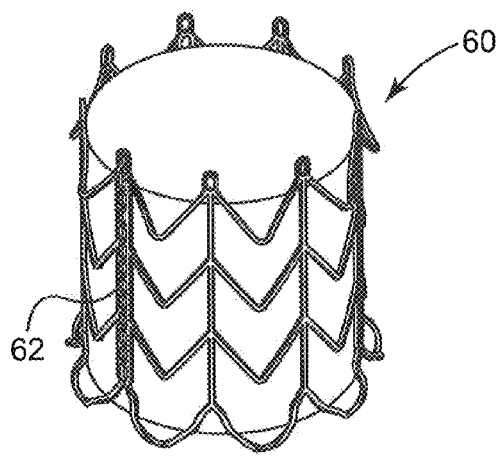
FIG. 5 is a perspective view of an embodiment of a stent in accordance with the invention.
Figure 6:
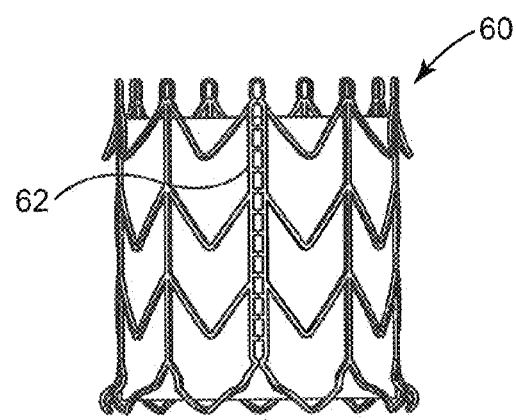
FIG. 6 is a front view of the stent of FIG. 5.
Figure 8:
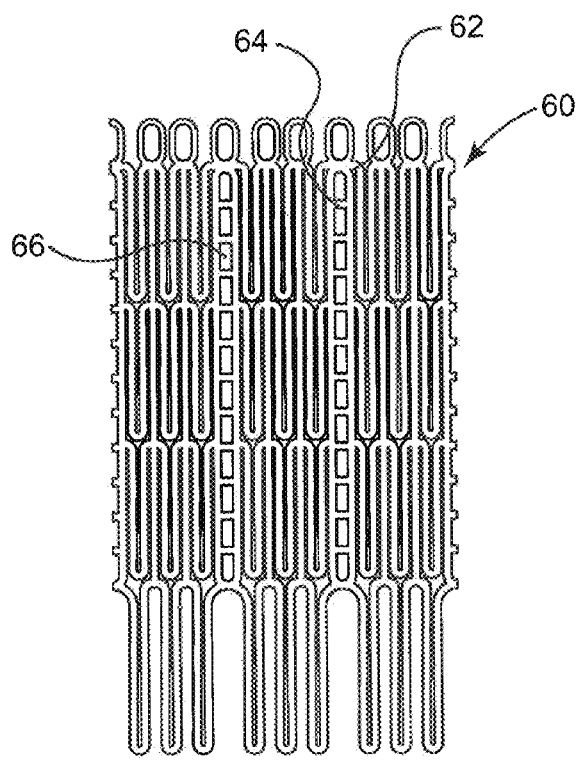
FIG. 8 is a top view a cutting pattern for the stent of FIG. 5.
Figure 7:
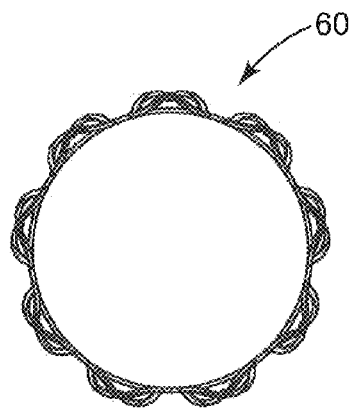
FIG. 7 is a top view of the stent of FIG. 5.

FIG. 4 illustrates an exemplary laser cutting pattern that can be used to form the stent 10 out of a tube or single sheet of material. The stent 10 can alternatively be made from multiple components that are attached to each other and formed into a tubular shape. However, if the stent will be cut from a tube or single sheet of material as shown, the various structures will be designed so that they do not interfere with each other in the pattern.

Figure 26:
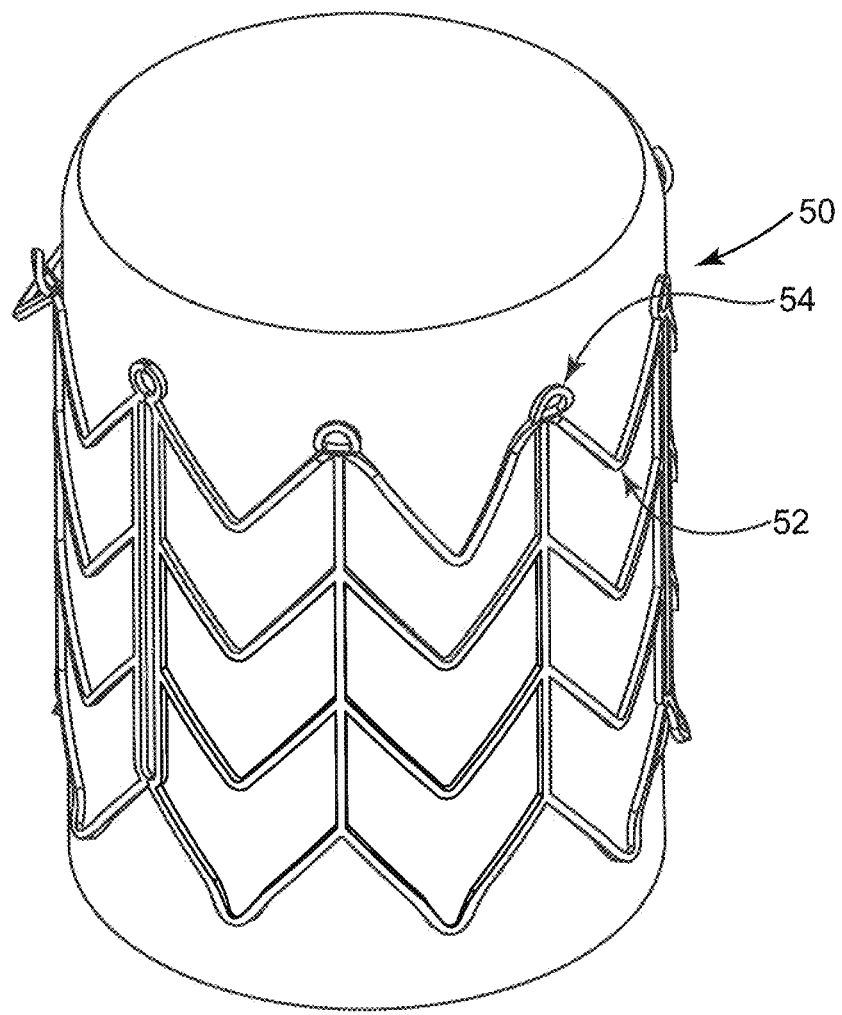
FIG. 26 is a perspective view of another stent embodiment of the invention.

FIG. 26 illustrates another exemplary embodiment of a stent 50 positioned for clarity on a mandrel, which also may be referred to as a sub-coronary stent in that it is preferably relatively short (e.g., 25 mm long) to enable stent placement below the coronary arteries in the aorta. This stent includes a number of the same features as the stent of FIGS. 1-4, although this stent 50 does not include the integrated petals shown and described above relative to stent 10. Rather, the V-shaped structures 52 at the outlet end of the stent 50 are generally in the same plane as the tubular outer shape of the stent 50 (i.e., the structures 52 are not flared outwardly). The stent 50 also includes eyelets 54 at the outlet end of the stent, which can be in the same general plane as the outer tubular shape of the stent 50, or they can be directed at least slightly inward or at least slightly outward relative to the outer tubular shape of the stent 50.

FIGS. 5-8 illustrate another exemplary embodiment of a stent 60, which is similar in structure to the stent 10 described above, including a wire structure with multiple commissure attachment posts 62. These posts 62 include two vertical struts that are spaced at least slightly from each other. These posts 62 further include multiple horizontal members 64 that are spaced from each other along the length or height of each post 62. The spaces or openings 66 that are created between the horizontal members 64 provide locations through which suture material, needles, and/or other fastening materials can be inserted for attachment of leaflet or valve material to the stent at the commissure posts. In addition, the horizontal members 64 can be used as defined anchoring points for the fastening materials. For example, a suture material can be inserted through a first opening 66 and then through another opening 66 in a predetermined pattern to stitch valve material to the commissure attachment posts 62. The horizontal members 64 can further be used as anchoring structures that keep sutures or other attachment mechanisms from moving vertically past a certain position along the attachment posts 62.

Figure 9:
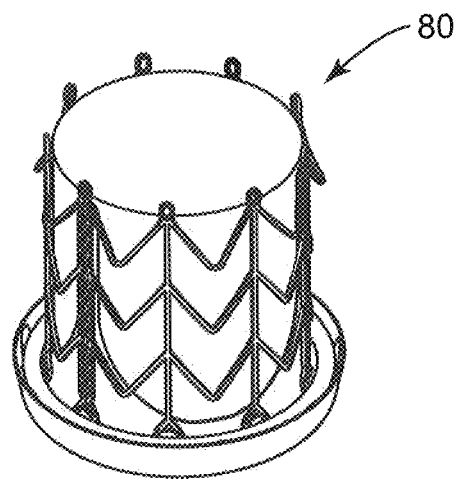
FIG. 9 is a perspective view of an embodiment of a stent in accordance with the invention.
Figure 10:
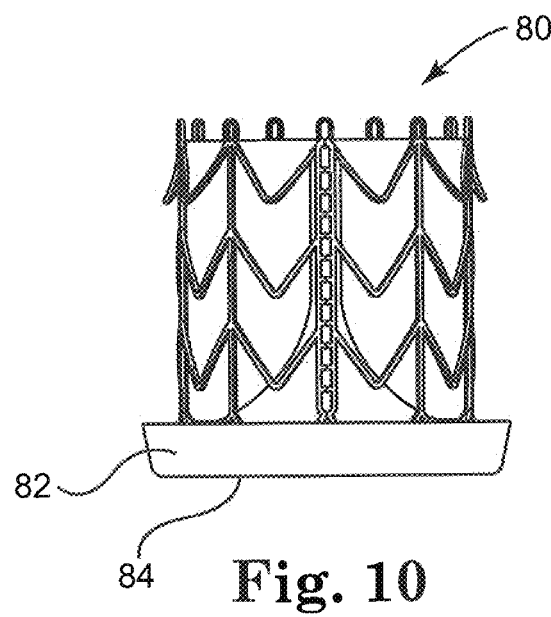
FIG. 10 is a front view of the stent of FIG. 9.
Figure 11:
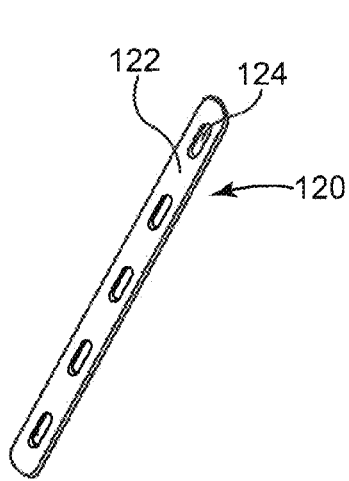
FIG. 11 is a perspective view of a "ladder" mechanism used for attachment of tissue to a stent.

Another embodiment of a stent 80 is illustrated in FIGS. 9 and 10, which has a similar structure to stent structures described above relative to tubular stent constructions. Stent 80 further includes a sealing skirt 82 at its inlet end 84. The sealing skirt 82 can provide for improved sealing between the stent 80 and the anatomy in which the stent 80 is placed, such as the annulus of a valve, for example. The sealing skirt 82 can be configured to unfurl away from the inlet end 84 of the valve and into the delivery system that was used to deliver the stent 80, if desired. In this way, the material used to make the sealing skirt 82 does not increase the overall size of the stent 80 when it is crimped or compressed. The sealing skirt 82 can further be provided with radiopaque, echogenic properties or other visually detectable properties so that an operator can assess the proper positioning of the stent 80 in the patient's anatomy prior to releasing it from the delivery system.

A number of systems, components, and devices are described below for attachment of valve material (e.g., tissue leaflets) within the interior area of a stent structure. It is understood that the systems that are shown and described herein for this purpose can be used with stent configurations described above and/or other stent constructions.

In one exemplary embodiment, a tubular stent structure includes at least one commissure post, along with a first leaflet and a second leaflet. Leaflets are attached or sewn to the post using suture material. In this embodiment, a tissue "cushion" is provided on both sides of the commissure attachment post to help absorb and distribute stress away from the stitch points and to minimize tissue abrasion that can be caused without such protection. In this configuration, the leaflets 104, 106 can flex along the tissue and the leaflet/tissue seam line and the tissue cushion distributes stress from flexing during opening and closing of leaflets away from the suture points where leaflets are attached into the attachment post.

Another configuration and device that can be used in the attachment of valve material to a stent structure is shown and described relative to FIGS. 11-14. In particular, a relatively rigid "ladder" member 120 is provided to support the leaflet commissure area and transfer the line or point about which the leaflets 140 flex or bend to a location that is spaced from the suture line. In this way, the stresses can be more evenly distributed and durability of the valve improved. Ladder member 120 includes a relatively flat elongated plate 122 having multiple holes or openings 124 along its length. In order to minimize or prevent damage to the tissue of the valve, the corners and edges of the ladder member 120 are preferably rounded or smoothed. The holes 124 are preferably spaced from each other by a distance that corresponds with a desired stitching pattern that will be used to both secure the member 120 to the stent structure and attach the leaflets. It is further contemplated that the ladder member 120 is configured to match specific commissure features of the stent.

Figure 12:
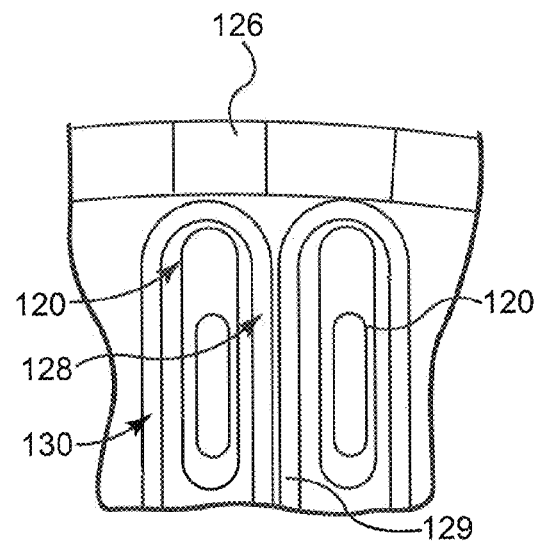
FIG. 12 is a top view of two ladder mechanisms of FIG. 11 positioned relative to leaflets and a stent.
Figure 13:
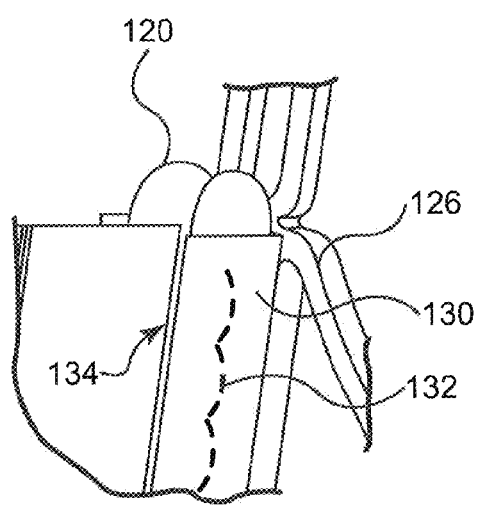
FIG. 13 is a perspective view of the ladder mechanisms, tissue, and portion of a stent illustrated in FIG. 12.

FIGS. 12 and 13 illustrate two ladder members 120 positioned relative to a portion of a stent 126 and portions of two leaflets. In particular, portions 128, 129 of adjacent leaflet commissures are secured in the space between two ladder members 120. The ladder members 120 are spaced from each other by a distance that allows the components to be securely fastened to each other, but that accommodates the thickness of the leaflets that are positioned between them. Additional material from the leaflets extends around the ends of the ladder members 120 between the edge of the ladder members 120 and the stent 126, then along the outwardly facing sides of the ladder members 120, such as is indicated by the reference number 130. This additional material provides for improved security in tissue attachment and also provides additional attachment locations.

Figure 15:
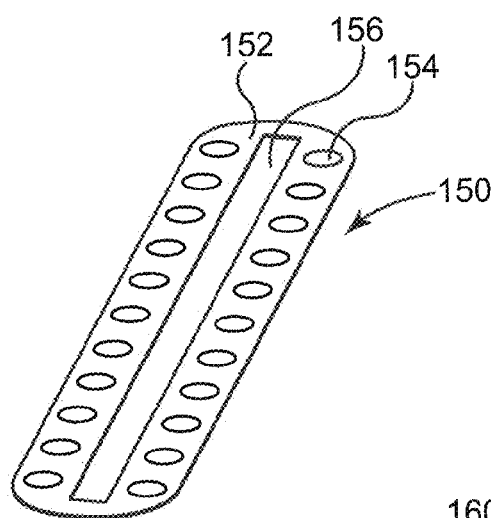
FIG. 15 is a perspective view of a "slot bar" mechanism used for attachment of tissue to a stent.

Sutures 132 can be inserted through the tissue material to secure it to the ladder members 120, where one exemplary stitching pattern is illustrated in FIG. 15. An appropriate number of stitches should be made through the tissue material and ladder member 120 to securely attach the ladder members 120 to the leaflets. The same or a different suture material can be used to attach or position adjacent ladder members 120 relative to each other. Additional sutures or an extension of the sewing pattern can also be used to connect the ladder members 120 to the stent 126. The suture pattern can follow the holes in the ladder member 120 such that the ladder member 120 provides a template for sewing the leaflet tissue to the ladder members 120, or an alternate stitching pattern can be used. The leaflets can then flex against a long vertical edge 134 of each of the ladder members 120, thereby transferring the stress away from the attachment suture line.

Figure 14:
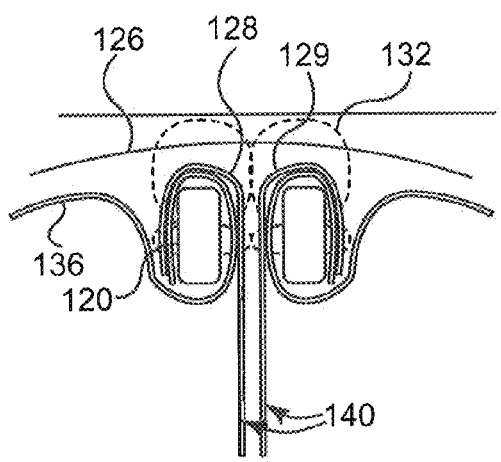
FIG. 14 is a top schematic view of the stent arrangement of FIGS. 12 and 13.

FIG. 14 illustrates another tissue attachment arrangement that includes the use of two ladder members 120, as described above, along with additional protective layers 136. Each protective layer 136 can provide supplemental padding between a ladder and the adjacent leaflet material, and can also provide additional strength at the attachment sites. The protective layers 136 can be made of a material such as cloth, tissue, polymeric sheets, or the like. As shown, one protective layer 136 is used for each of the ladder members 120, with the protective layer 136 being positioned between each ladder member 120 and its corresponding leaflet 128, 129. Each protective layer 136 can wrap around at least a portion of the periphery of its corresponding ladder member 120, and in one embodiment will wrap around almost the entire periphery of the ladder members 120, as shown. Further, each protective layer 136 can extend along the entire length or height of its corresponding ladder 120, or it may extend along only a portion of the length of the ladder member 120. An exemplary pattern of stitching the components to each other and to the stent 126 is illustrated with the sutures 132 (shown as broken lines), although a different stitching pattern can instead be used.

Figure 16:
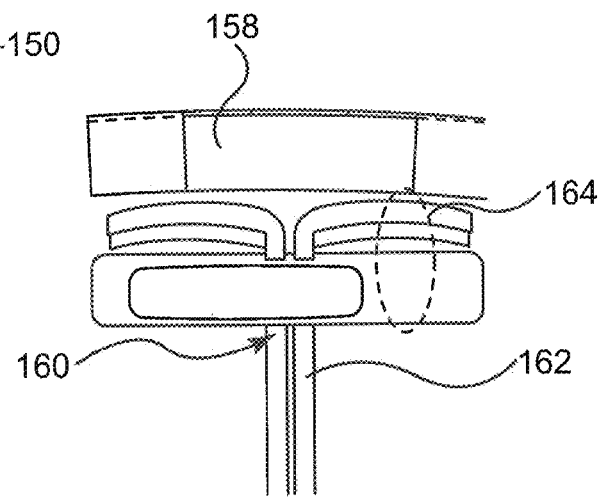
FIG. 16 is a top view of a slot bar mechanism of FIG. 15 positioned relative to leaflets and a stent.
Figure 17:
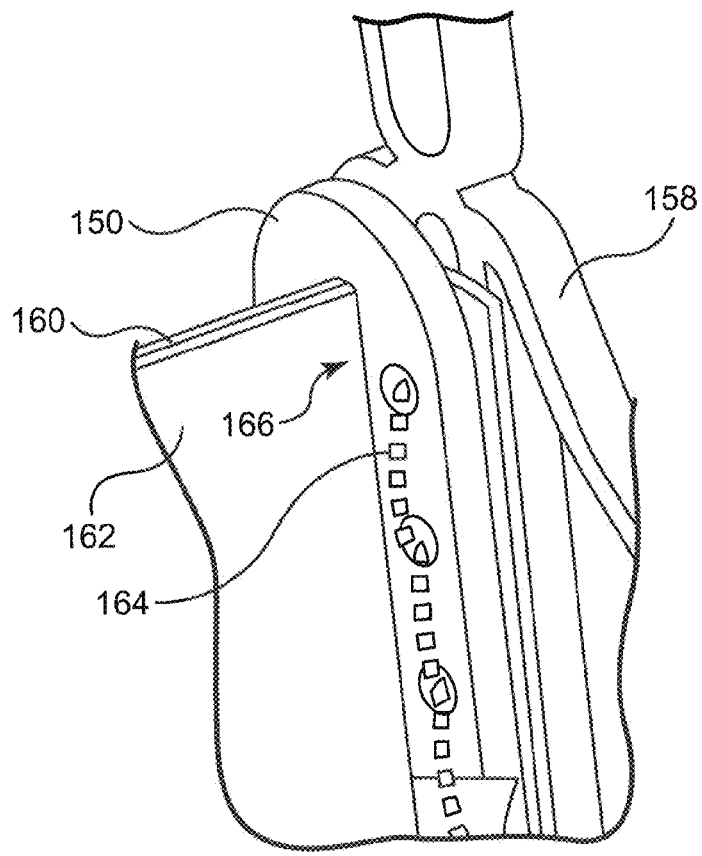
FIG. 17 is perspective view of the slot bar mechanism, tissue, and portion of a stent illustrated in FIG. 16.

Another configuration and device that can be used in the attachment of valve material to a stent structure is shown and described relative to FIGS. 15-17. In particular, a relatively rigid "slot bar" member 150 is provided to support the leaflet commissure area and transfer the line or point about which the leaflets flex or bend to a location that is spaced from the suture line. In this way, the stresses can be more evenly distributed. Slot bar member 150 includes a relatively flat elongated plate 152 having a longitudinal slot 156 extending along a portion of its length, and multiple holes or openings 154 along the length of the member 150 on both sides of the slot 156. Alternatively, one or both ends could be open and/or two separate portions can make up the slot bar member. In order to minimize or prevent damage to the tissue of the valve, the corners and edges of the slot bar member 150 are preferably rounded or smoothed. The holes 154 are preferably spaced from each other by a distance that corresponds with a desired stitching pattern that will be used to both secure the member 150 to the stent structure and the tissue to the slot bar. It is further contemplated that the slot bar member 150 is configured to match specific commissure features of the stent to which it will be attached. In addition, the width of the slot 156 is preferably selected based on the thickness of the leaflets that will be inserted through the slot 156. Thus, the slot 156 should be wide enough to accommodate two thicknesses of leaflet material; however, the slot 156 may be designed for more layers of material or for an optimized compression fit, if desired. In order to provide secure positioning of the tissue layers within the slot 156 and to minimize the potential for the tissue to be pulled from the slot 156, the slot should not be substantially wider than the thickness of the materials that will be positioned within it.

FIGS. 16-17 illustrate slot bar member 150 positioned relative to a portion of a stent 158 and portions of two leaflets 160, 162. In particular, the end portions of adjacent leaflet commissures 160, 162 are pulled through the slot 156 by a sufficient distance that the free edge of each of the leaflets extends at least slightly past the holes 154 on the flat side of the plate 152. This end portion of the leaflets 160, 162 will thereby be positioned between the slot bar member 150 and the stent to which they will be attached. In this way, the leaflets 160, 162 can be securely fastened to the slot bar member 150 and the stent 158. Sutures 164 can then be inserted through the tissue material to secure it to the slot bar member 150, where one exemplary stitching pattern is illustrated in FIGS. 16 and 17. The stitching pattern can follow the holes 154 in the slot bar member 150 such that the slot bar member 150 provides the template for sewing the leaflet tissue to the slot bar member 150, or an alternate stitching pattern can be used. The sutures 164 can thereby connect the slot bar member 150 to the leaflets 160, 162. Additional sutures or the same sutures can also be used to connect the slot bar member 150 to the stent 158. The leaflets 160, 162 can then flex over a long vertical edge 166 on each side of the slot bar member 150 during valve leaflet opening and closing, thereby transferring the stress away from the attachment suture line and increasing the durability of the valve.

Figure 18:
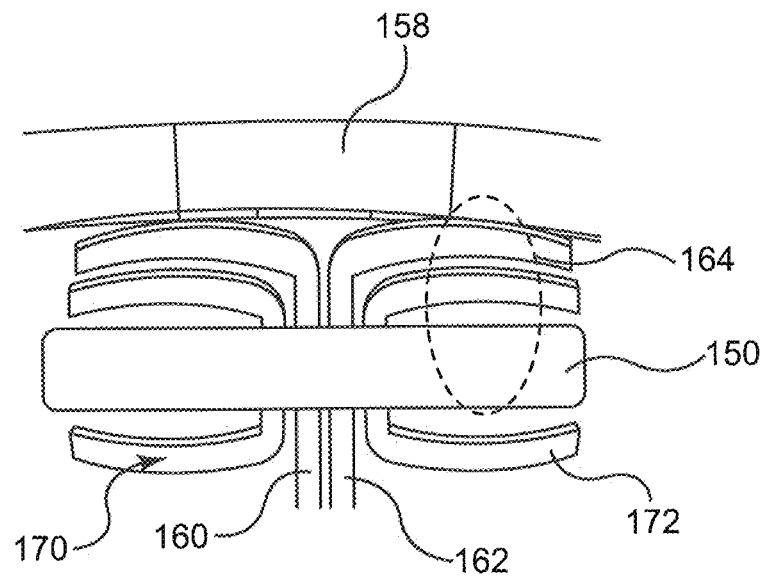
FIG. 18 is a top view of a "padded slot bar" mechanism positioned relative to leaflets and a stent.
Figure 19:
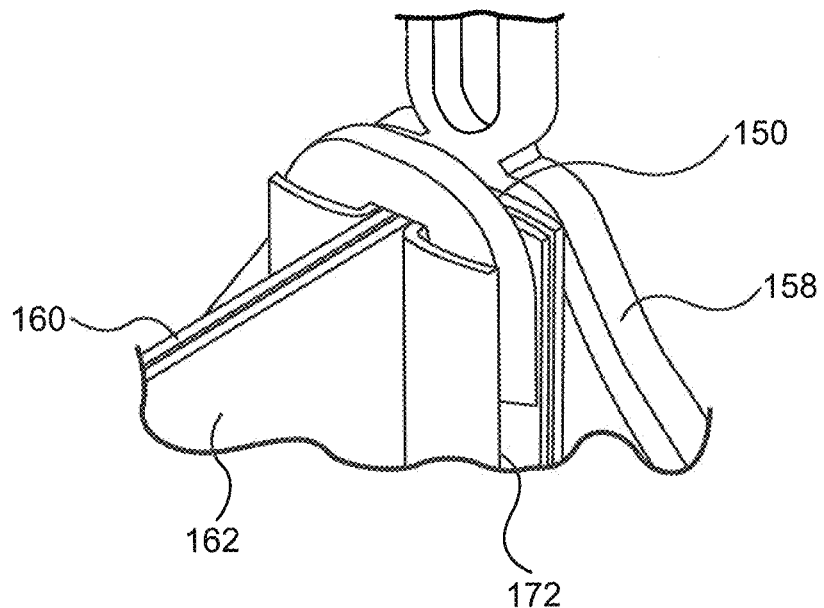
FIG. 19 is a perspective view of the padded slot bar mechanism, tissue, and portion of a stent illustrated in FIG. 18.

FIGS. 18 and 19 illustrate another tissue attachment arrangement that includes the use of a slot bar member 150 of the type described above, along with additional protective members 170, 172. Protective members 170, 172 are positioned on opposite sides of the slot 156 of the slot bar member 150 so that each of the members 170, 172 can protect one of the leaflets 160, 162. Each protective member 170, 172 can provide additional padding or cushioning between one of the leaflets 160, 162 and the slot bar member 150 during opening and closing of the leaflets. The protective members 170, 172 can be made of a material such as cloth, tissue, polymeric sheets, or the like. Further, each protective member 170, 172 can extend along the entire length of its corresponding slot bar member 150, or it may extend along only a portion of the length of the slot bar member 150. An exemplary pattern of stitching the components to each other and to the stent 158 is illustrated with the schematic representation of a suture 164, although a different stitching pattern can instead be used. The suture material can be used to attach the excess tissue material to only the slot bar member 150, if desired. Alternatively, the protective members on the leaflet side of the slot bar member could be extended circumferentially beyond the slot bar member and attached to the stent (not shown). In this way, the leaflet would be prevented from contacting the suture material during opening of the valve reducing the potential for leaflet abrasion and tearing. In order to accommodate the thickness of the extra layers provided by the protective members 170, 172, the slot 156 should have an appropriate width.

Figure 20:
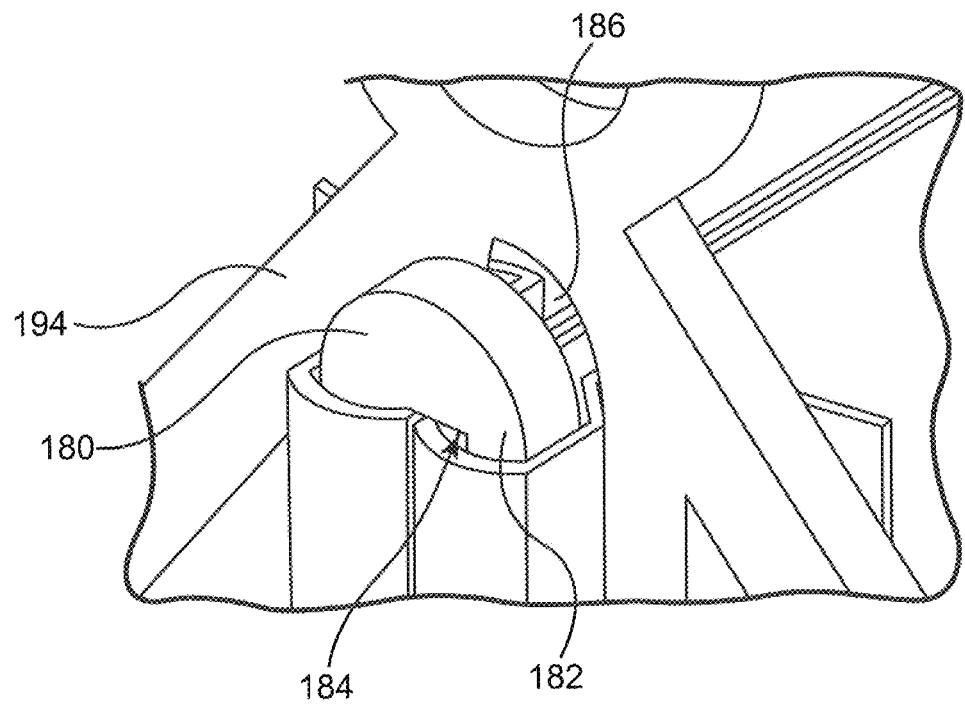
FIG. 20 is a perspective view of a "buckle" mechanism positioned relative to leaflets and a stent.
Figure 21:
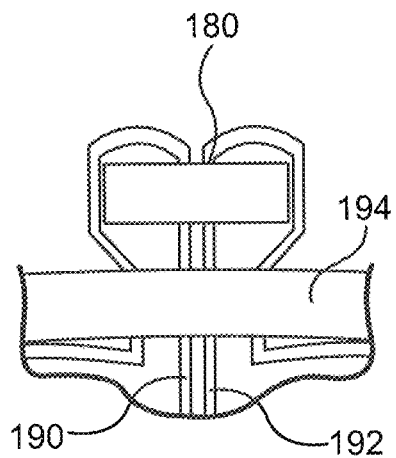
FIG. 21 is a top view of the portion of a stent, leaflets, and buckle mechanism illustrated in FIG. 20.
Figure 22:
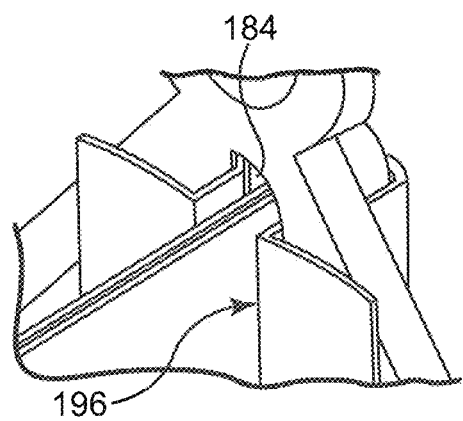
FIG. 22 is another perspective view of the portion of a stent illustrated in FIG. 20.

Another configuration and device that can be used in the attachment of valve material to a stent structure is shown and described relative to FIGS. 20-22. In particular, a relatively rigid "buckle" member 180 is provided to support the leaflet commissure area and transfer the line or point about which the leaflets flex or bend to a location that is spaced away from the suture line. In this way, the stresses can be more evenly distributed increasing the durability of the valve. Buckle member 180 includes a relatively flat elongated plate 182 having a longitudinal slot 184 extending along a portion of its length. The slot could alternatively be open at either one or both ends of the plate. In order to minimize or prevent damage to the tissue of the valve, the corners and edges of the buckle member 180 are preferably rounded or smoothed. The width of the slot 184 is preferably selected based on the thickness of the layers of material that will be inserted through the slot 184. Thus, the slot 184 should be wide enough to accommodate the two thicknesses of leaflet material that will extend through it, as described below; however, the slot 184 may be designed for more layers of material or for an optimized compression fit, if desired. In order to provide secure positioning of the tissue layers within the slot 184 and to minimize the potential for the tissue to be pulled from the slot 184, the slot should not be substantially wider than the width of the material that will be positioned within it.

As shown in the Figures, the buckle member 180 is positioned on the opposite side of a stent 194 than the other embodiments discussed above (i.e., on the outer side of the stent structure rather than on the inner side of the stent structure). In this embodiment, the stent 194 has a vertical slot 186 in its commissure post that generally corresponds to the slot 184 in the buckle member 180. The end portions of two leaflets 190, 192 are pulled through the slot 186 in the stent commissure post, then through the slot 184 in the buckle member 180. The ends of the leaflets are then wrapped around the back side of the buckle member 180 and pulled back through the slot 186 in the commissure post in the opposite direction than the first insertion of the leaflets through this slot 186. The leaflets 190, 192 should continue to be pulled through the slot 186 by a sufficient distance that the free edge of each of the leaflets 190, 192 extends at least slightly past the structure of the stent in the internal area of the stent. With this arrangement, the leaflets 190, 192 will flex generally along a vertical line 196, which is the tissue that covers a vertical edge of the stent. In this embodiment, no sutures are required for attachment of the leaflets 190, 192 to the stent and/or the buckle member 180. Rather, the force on the commissure caused by the closing of the leaflets 190, 192 will cause the buckle member 180 to be pressed toward the stent, thereby compressing and locking the excess tissue material between the buckle member and the stent. This secures the commissure and prevents the tissue material of the leaflets from pulling out of the assembly.

Figure 23:
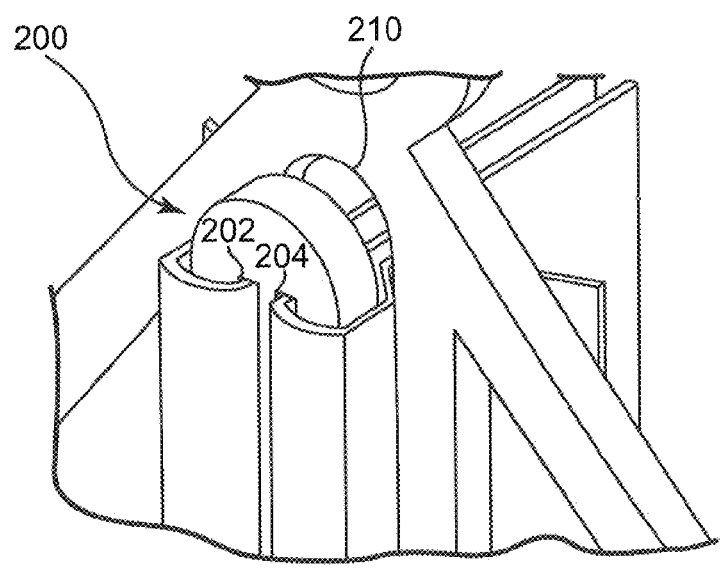
FIG. 23 is a perspective view of a "padded buckle" mechanism positioned relative to leaflets and a stent.
Figures 24, 25:
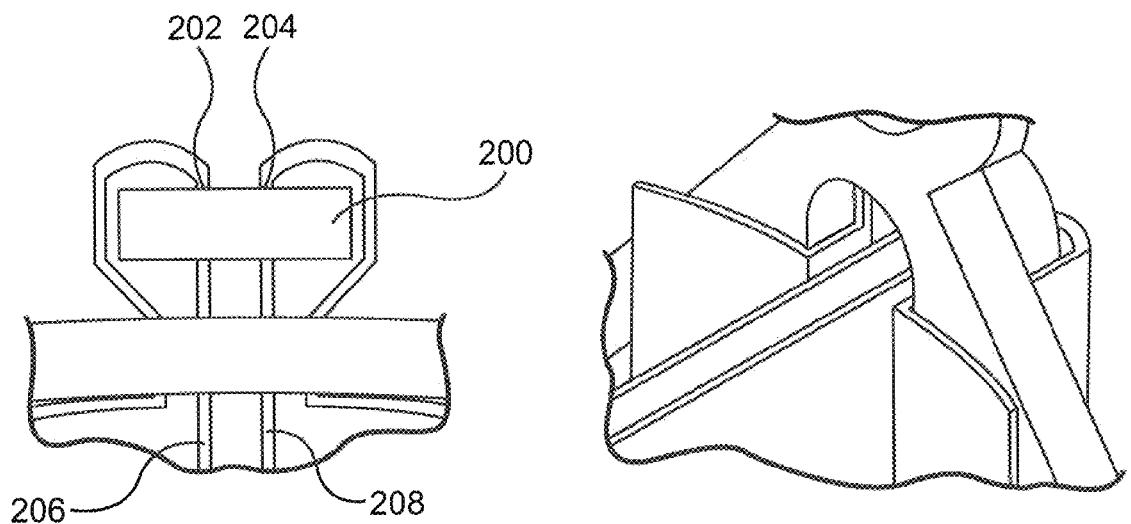
FIG. 24 is a top view of the portion of a stent, leaflets, and padded buckle mechanism illustrated in FIG. 23.
FIG. 25 is another perspective view of the portion of a stent illustrated in FIG. 23.

FIGS. 23-25 illustrate another configuration and device for the attachment of valve material to a stent structure that includes the use of a buckle member 200 that is similar in design and operation to the buckle member 180 discussed above. In this embodiment, however, the buckle member 200 includes two longitudinal slots 202, 204 that are spaced from each other across the width of the buckle member 200, rather than a single, central slot. In this way, a first leaflet 206 can be pulled through a longitudinal slot 210 in the stent and through longitudinal slot 202 of the buckle member 200, and a second leaflet 208 can be pulled through a longitudinal slot 210 in the stent and through longitudinal slot 204 of the buckle member 200. The leaflets 206, 208 can then be wrapped around the back side of the buckle member 200, pulled back through the longitudinal slot 210 in the commissure post, and pulled through the slot by a sufficient distance that the leaflets can be secured to the stent without stitching, similar to the arrangement that uses the buckle member 180.

It is noted that in many of the stent embodiments shown and described herein, the aspect ratio of certain portions of the stent can be somewhat different from that shown. Further, stent embodiments described herein may be modified to include additional structure for attachment of tissue for the valve, such as the vertical stent posts described in many of the embodiments.

Delivering any balloon-expandable stents of the invention to the implantation location can be performed percutaneously. In general terms, this includes providing a transcatheter assembly, including a delivery catheter, a balloon catheter, and a guide wire. Some delivery catheters of this type are known in the art, and define a lumen within which the balloon catheter is received. The balloon catheter, in turn, defines a lumen within which the guide wire is slideably disposed. Further, the balloon catheter includes a balloon that is fluidly connected to an inflation source. It is noted that if the stent being implanted is the self-expanding type of stent, the balloon would not be needed and a sheath or other restraining means would be used for maintaining the stent in its compressed state until deployment of the stent, as described herein. In any case, for a balloon-expandable stent, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of the transcatheter assembly.

Prior to delivery, the stent is mounted over the balloon in a contracted state to be as small as possible without causing permanent deformation of the stent structure. As compared to the expanded state, the support structure is compressed onto itself and the balloon, thus defining a decreased inner diameter as compared to an inner diameter in the expanded state. While this description is related to the delivery of a balloon-expandable stent, the same basic procedures can also be applicable to a self-expanding stent, where the delivery system would not include a balloon, but would preferably include a sheath or some other type of configuration for maintaining the stent in a compressed condition until its deployment.

With the stent mounted to the balloon, the transcatheter assembly is delivered through a percutaneous opening (not shown) in the patient via the delivery catheter. The implantation location is located by inserting the guide wire into the patient, which guide wire extends from a distal end of the delivery catheter, with the balloon catheter otherwise retracted within the delivery catheter. The balloon catheter is then advanced distally from the delivery catheter along the guide wire, with the balloon and stent positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the invention, the stent includes a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

Once the stent is properly positioned, the balloon catheter is operated to inflate the balloon, thus transitioning the stent to an expanded state. Alternatively, where the support structure is formed of a shape memory material, the stent can self-expand to its expanded state.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A stented valve comprising:
    a stent structure comprising a generally tubular body portion having a first end, a second end, an interior area, a longitudinal axis, and a plurality of vertical wires extending generally parallel to the longitudinal axis around a periphery of the body portion, wherein the plurality of vertical wires includes multiple commissure structures and at least one structural wire positioned between adjacent commissure structures, wherein at least one of the commissure structures comprises two vertical wires spaced circumferentially from each other along a majority of a length of the longitudinal axis of the tubular body, and at least three rows of V-shaped wire structures having a first end, a second end, and a peak between the first and second ends, wherein a first end of each V-shaped structure extends from a first vertical wire and a second end of each V-shaped structure extends from a second vertical wire that is adjacent to the first vertical wire, wherein the at least three rows of V-shaped structures are oriented so that their peaks are facing in the same direction relative to the first and second ends of the body portion;
    a valve structure comprising a plurality of leaflets;
    at least one leaflet attachment element comprising an elongated plate for securing the plurality of leaflets to the stent structure, wherein the elongated plate comprises a first longitudinal slot; and
    at least one protective member positioned between the elongated plate and the leaflets when the leaflets extend through the first longitudinal slot.

2. The stented valve of claim 1, wherein each leaflet is attached at a first end to a first commissure structure and is attached at a second end to a second commissure structure.

3. The stented valve of claim 1, wherein each of the V-shaped structures of each row is axially spaced along the longitudinal axis from an adjacent V-shaped structure.

4. The stented valve of claim 3, wherein a first V-shaped structure of each row is positioned adjacent to a first end of the tubular body and wherein the peak of each of the first V-shaped structures is angled at least slightly outward relative to the tubular body.

5. The stented valve of claim 1, wherein all of the rows of V-shaped structures around the periphery of the tubular body have the same number of V-shaped structures.

6. The stented valve of claim 5, wherein the first end of each V-shaped structure in a first row is positioned in the same vertical location along the vertical wire from which it extends as the second end of each V-shaped structure in an adjacent row.

7. The stented valve of claim 1, wherein a first end of each vertical wire comprises an eyelet.

8. The stented valve of claim 7, wherein at least one of the eyelets is angled at least slightly relative to the longitudinal axis of the tubular body.

9. The stented valve of claim 4, wherein a second V-shaped structure of each row is positioned adjacent to a second end of the tubular body and wherein the peak of each of the second V-shaped structures is angled at least slightly outward relative to the tubular body.

10. The stented valve of claim 1, wherein the plurality of vertical wires comprises three commissure structures spaced from each other around the periphery of the tubular body and two structural wires between each pair of adjacent commissure structures.

11. The stented valve of claim 1, wherein the peak of each V-shaped structure is directed toward an inlet end of the stent structure.

12. The stented valve of claim 1, further comprising a plurality of horizontal members spaced from each other and extending from the two vertical wires of each commissure structure.

13. The stented valve of claim 11, further comprising a sealing skirt at the inlet end of the stent structure, wherein the sealing skirt extends around at least a portion of the circumference of the tubular body.

14. The stented valve of claim 1, comprising four rows of V-shaped wire structures.

15. The stented valve of claim 1, wherein the elongated plate is positioned within the interior area of the stent.

16. The stented valve of claim 15, wherein a first and second leaflet extend through the first longitudinal slot and are secured to the elongated plate, and wherein the elongated plate is secured to the stent.

17. The stented valve of claim 1, wherein the elongated plate is positioned on an exterior side of the stent, and wherein a first and second leaflet extend between the two vertical wires of the commissure structure, through the longitudinal slot of the elongated plate, around a corresponding outer edge of the elongated plate, and back through the two vertical wires of the commissure structure.

18. The stented valve of claim 1, wherein the elongated plate is positioned on an exterior of the stent, the elongated plate further comprising a second longitudinal slot, wherein a first leaflet extends between the two vertical wires of the commissure structure, through the first longitudinal slot of the elongated plate, around a corresponding outer edge of the elongated plate, and back through the two vertical wires of the commissure structure, and wherein a second leaflet extends between the two vertical wires of the commissure structure, through the second longitudinal slot of the elongated plate, around a corresponding outer edge of the elongated plate, and back through the two vertical wires of the commissure structure.

19. The stented valve of claim 1, wherein the elongated plate further comprises a plurality of openings.

* * * * *